US011213432B2

(12) United States Patent
Potters

(10) Patent No.: US 11,213,432 B2
(45) Date of Patent: Jan. 4, 2022

(54) TRANSPARENT COVER DRESSING APPLICATION SYSTEM AND INCLUSION OF LABEL STRIP

(71) Applicant: Avery Dennison Corporation, Glendale, CA (US)

(72) Inventor: Pieter Potters, Turnhout (BE)

(73) Assignee: Avery Dennison Corporation, Glendale, CA (US)

( * ) Notice: Subject to any disclaimer, the term of this patent is extended or adjusted under 35 U.S.C. 154(b) by 553 days.

(21) Appl. No.: 14/776,834

(22) PCT Filed: Mar. 13, 2014

(86) PCT No.: PCT/US2014/025549
§ 371 (c)(1),
(2) Date: Sep. 15, 2015

(87) PCT Pub. No.: WO2014/151355
PCT Pub. Date: Sep. 25, 2014

(65) Prior Publication Data
US 2016/0030248 A1 Feb. 4, 2016

Related U.S. Application Data

(60) Provisional application No. 61/787,908, filed on Mar. 15, 2013.

(51) Int. Cl.
*A61F 13/02* (2006.01)
*A61F 13/00* (2006.01)
(52) U.S. Cl.
CPC ...... *A61F 13/023* (2013.01); *A61F 13/00055* (2013.01); *A61F 13/00059* (2013.01);
(Continued)

(58) Field of Classification Search
CPC .............. A61F 13/023; A61F 13/00055; A61F 13/00059; A61F 13/00085; A61F 13/0259;
(Continued)

(56) References Cited

U.S. PATENT DOCUMENTS 2,736,721 A   2/1956   Dexter
4,199,567 A   4/1980   Rankin
(Continued)

FOREIGN PATENT DOCUMENTS

AU   1985043241   12/1985
CA   1207228      7/1986
(Continued)

OTHER PUBLICATIONS

Giunchedi, et al. "Formulation and in vivo evaluation of chlorhexidine buccal tablets prepared using drug-loaded chitosan microspheres," European Journal of Pharmaceutics and Biopharmaceutics, Elsevier Science Publishers B.V., Amsterdam, NL, vol. 53, No. 2, Mar. 1, 2002, pp. 233-239, XP004342819, ISSN: 0939-6411, DOI: 10.1016/S0939-6411(01)00237-5 Section 2.2 Preparation by spray-drying; table 2.
(Continued)

*Primary Examiner* — Ophelia A Hawthorne

(57) ABSTRACT

A dressing having a multilayer assembly in which dressing includes a polyurethane dressing layer that is adhesively secured over a wound or other location on a user's skin. Label strips that can be incorporated into the dressing. The label strips can include text, indicia, logos, or other markings which are applied to the strip prior to or after application of the dressing.

11 Claims, 3 Drawing Sheets

(52) U.S. Cl.
CPC .... *A61F 13/00085* (2013.01); *A61F 13/0259* (2013.01); *A61F 2013/00153* (2013.01); *A61F 2013/00182* (2013.01); *A61F 2013/00846* (2013.01); *A61F 2013/00851* (2013.01)

(58) Field of Classification Search
CPC .. A61F 2013/00153; A61F 2013/00182; A61F 2013/00846; A61F 2013/00851; A61F 13/02; A61F 2013/00868; A61L 15/58; A61L 15/26
See application file for complete search history.

(56) References Cited

U.S. PATENT DOCUMENTS

| | | | |
|---|---|---|---|
| 4,310,509 A | | 1/1982 | Berglund et al. |
| 4,434,181 A | | 2/1984 | Marks, Sr. et al. |
| 4,460,369 A | | 7/1984 | Seymour |
| 4,600,001 A | * | 7/1986 | Gilman ............ A61F 13/023 602/52 |
| 4,753,232 A | * | 6/1988 | Ward ............... A61F 13/023 602/52 |
| 4,941,882 A | | 7/1990 | Ward et al. |
| 4,990,144 A | | 2/1991 | Blott |
| 5,018,516 A | * | 5/1991 | Gilman ............ A61F 13/023 602/52 |
| 5,069,907 A | | 12/1991 | Mixon et al. |
| 5,214,119 A | | 5/1993 | Leir et al. |
| 5,270,358 A | | 12/1993 | Asmus |
| 5,322,695 A | | 6/1994 | Shah et al. |
| 5,340,581 A | | 8/1994 | Tseng et al. |
| 5,382,451 A | | 1/1995 | Johnson et al. |
| 5,389,376 A | | 2/1995 | Duan et al. |
| 5,441,741 A | | 8/1995 | Cheong |
| 5,614,310 A | | 3/1997 | Delgado et al. |
| 5,686,096 A | | 11/1997 | Khan et al. |
| 5,702,721 A | | 12/1997 | Horstmann et al. |
| 5,717,005 A | | 2/1998 | Richardson |
| 5,763,412 A | | 6/1998 | Khan et al. |
| 5,908,693 A | | 6/1999 | Delgado et al. |
| 6,043,406 A | * | 3/2000 | Sessions ........... A61F 13/023 602/41 |
| 6,228,354 B1 | | 5/2001 | Jeng |
| 6,455,086 B1 | | 9/2002 | Trinh et al. |
| 6,458,341 B1 | | 10/2002 | Rozzi et al. |
| 6,495,158 B1 | | 12/2002 | Buseman et al. |
| 6,518,359 B1 | | 2/2003 | Clemens et al. |
| 6,565,873 B1 | | 5/2003 | Shefer et al. |
| 6,589,562 B1 | | 7/2003 | Shefer et al. |
| 6,599,525 B2 | | 7/2003 | Scamilla Aledo et al. |
| 6,642,304 B1 | | 11/2003 | Hansen et al. |
| 6,733,745 B2 | | 5/2004 | Rozzi et al. |
| 6,742,522 B1 | * | 6/2004 | Baker ............... A61B 46/00 128/849 |
| 6,844,306 B2 | | 1/2005 | Werle et al. |
| 6,893,655 B2 | | 5/2005 | Flanigan et al. |
| 7,160,976 B2 | | 1/2007 | Luhmann et al. |
| 7,674,473 B2 | | 3/2010 | Falder et al. |
| 7,683,216 B2 | | 3/2010 | Dubois et al. |
| 7,704,523 B2 | | 4/2010 | Serafica et al. |
| 7,824,122 B2 | | 11/2010 | Flores et al. |
| 8,623,935 B2 | | 1/2014 | Hobbs et al. |
| 8,969,649 B2 | | 3/2015 | Leibowitz et al. |
| 9,101,134 B2 | | 8/2015 | Huang et al. |
| 9,278,155 B2 | | 3/2016 | Asmus et al. |
| 9,346,981 B2 | | 5/2016 | Wibaux et al. |
| 9,592,161 B2 | | 3/2017 | Rule et al. |
| 9,764,059 B2 | | 9/2017 | Wibaux et al. |
| 9,801,902 B2 | | 10/2017 | Smith et al. |
| 10,329,384 B2 | | 6/2019 | Hansen et al. |
| 10,456,498 B2 | | 10/2019 | Wibaux |
| 2002/0018814 A1 | | 2/2002 | Werle et al. |
| 2002/0072480 A1 | | 6/2002 | Werle et al. |
| 2003/0077316 A1 | | 4/2003 | Nichols et al. |
| 2003/0212005 A1 | | 11/2003 | Petito |
| 2004/0009202 A1 | | 1/2004 | Woller |
| 2004/0063792 A1 | | 4/2004 | Khera et al. |
| 2004/0109869 A1 | | 6/2004 | Glenn et al. |
| 2004/0170794 A1 | | 9/2004 | Verhaert |
| 2004/0241214 A1 | | 12/2004 | Kirkwood et al. |
| 2005/0049365 A1 | | 3/2005 | Cleary et al. |
| 2005/0118246 A1 | | 6/2005 | Wong et al. |
| 2005/0244346 A1 | | 11/2005 | Nakao et al. |
| 2005/0249791 A1 | | 11/2005 | Hobbs et al. |
| 2007/0116729 A1 | | 5/2007 | Palepu |
| 2007/0259029 A1 | | 11/2007 | McEntire et al. |
| 2008/0220045 A1 | | 9/2008 | Shalaby et al. |
| 2008/0233177 A1 | | 9/2008 | Meconi |
| 2009/0130157 A1 | | 5/2009 | Ylitalo et al. |
| 2010/0022654 A1 | | 1/2010 | Asmus et al. |
| 2010/0029779 A1 | | 2/2010 | Street et al. |
| 2010/0081672 A1 | | 4/2010 | Wan et al. |
| 2010/0303878 A1 | | 12/2010 | Slager et al. |
| 2010/0322996 A1 | | 12/2010 | Wibaux et al. |
| 2011/0067799 A1 | | 3/2011 | Mussig et al. |
| 2012/0078155 A1 | | 3/2012 | Bowman et al. |
| 2012/0245538 A1 | | 9/2012 | Horstmann et al. |
| 2012/0328682 A1 | | 12/2012 | Bardwell et al. |
| 2013/0072566 A1 | | 3/2013 | Asmus et al. |
| 2013/0239977 A1 | | 9/2013 | McGuire, Jr. |
| 2013/0243841 A1 | | 9/2013 | Kommareddy et al. |
| 2013/0303656 A1 | | 11/2013 | Wibaux et al. |
| 2014/0322299 A1 | | 10/2014 | Wibaux |
| 2015/0056291 A1 | | 2/2015 | Wibaux et al. |
| 2015/0367021 A1 | | 12/2015 | Wibaux |
| 2016/0000609 A1 | | 1/2016 | Van Holten et al. |
| 2016/0228600 A1 | | 8/2016 | Wibaux et al. |
| 2017/0007464 A1 | | 1/2017 | Liu et al. |
| 2017/0095431 A1 | | 4/2017 | Andrews et al. |
| 2020/0016291 A1 | | 1/2020 | Wibaux |

FOREIGN PATENT DOCUMENTS

| | | |
|---|---|---|
| CA | 2333009 | 12/1999 |
| CN | 1522687 | 8/2004 |
| CN | 1961666 | 5/2007 |
| CN | 101653431 | 2/2010 |
| EP | 0066899 A2 | 12/1982 |
| EP | 0404558 | 12/1990 |
| EP | 0328421 | 4/1993 |
| EP | 0361722 | 12/1993 |
| EP | 1139981 | 4/2002 |
| EP | 1203531 | 11/2003 |
| EP | 1784232 | 5/2007 |
| EP | 3280769 | 2/2018 |
| EP | 3368086 | 9/2018 |
| EP | 2968014 | 4/2019 |
| GB | 2274586 | 8/1994 |
| JP | 1990-147063 | 6/1990 |
| JP | 6-508287 | 9/1994 |
| JP | 6-509955 | 11/1994 |
| JP | 2825549 | 11/1998 |
| JP | 2002179513 | 6/2002 |
| JP | 2002-272831 | 9/2002 |
| JP | 2002-332228 | 11/2002 |
| JP | 2003534310 | 11/2003 |
| JP | 2004010545 | 1/2004 |
| JP | 2007502319 | 2/2007 |
| JP | 2007-526348 | 9/2007 |
| JP | 2007-536261 | 12/2007 |
| JP | 2014510038 | 4/2014 |
| WO | 1990/013780 | 11/1990 |
| WO | WO9300118 | 1/1993 |
| WO | WO1993002717 | 2/1993 |
| WO | WO9303649 | 3/1993 |
| WO | WO1999000025 | 1/1999 |
| WO | 1999023150 | 5/1999 |
| WO | WO992470 | 12/1999 |
| WO | WO2000/036353 | 6/2000 |
| WO | WO2000/061692 | 10/2000 |
| WO | 2003/103618 | 12/2003 |
| WO | 2004/080499 | 9/2004 |
| WO | 2009/064291 | 5/2009 |
| WO | WO2010080936 | 7/2010 |

(56) References Cited

FOREIGN PATENT DOCUMENTS

| WO | 2011/009083 | 1/2011 |
|---|---|---|
| WO | WO2011088072 | 7/2011 |
| WO | WO2012100244 | 7/2012 |
| WO | 2012/158483 | 3/2013 |
| WO | WO2013074628 | 5/2013 |
| WO | 2013/090191 | 6/2013 |
| WO | 2014/124232 | 8/2014 |
| WO | 2015/188031 | 12/2015 |
| WO | 2015187632 | 12/2015 |

OTHER PUBLICATIONS

International Search Report and Written Opinion issued in corresponding IA No. PCT/US2012/022162 dated Aug. 10, 2012.
Avery Dennison Medical Solutions Demonstrates the Efficacy of its new Chlorhexidine Gluconate Adhesive Delivery System, Avery Dennison Medical Solutions, Sep. 13, 2011, 1-2.
Boddupalli, et al., Mucoadhesive drug delivery system: An overview, Jounal of Advanced Pharmaceutical Technology & Research, vol. 1, 2010, 381-387.
Ceballos, et al., Influence of formulation and process variables on in vitro release of theophylline from directly-compressed Eudragit matrix tablets, II Farmaco, Jan. 15, 2005, 913-918, vol. 60, No. 11-12.
Cui, et al., Bilayer Films for Mucosal (Genetic) Immunization via the Buccal Route in Rabbits, Pharmaceutical Research, Jul. 2002, 947-953, vol. 19, No. 7.
Eudragit, acrylic polymers for solid oral dosage forms, Jan. 1, 2008, 1-11.
International Search Report and Written Opinion of the International Searching Authority, or the Declaration issued in corresponding IA No. PCT/US14/15263 dated Sep. 19, 2014.
International Search Report and Written Opinion of the International Searching Authority, or the Declaration issued in corresponding IA No. PCT/US2015/033689 dated Sep. 8, 2015.
International Search Report and Written Opinion of the International Searching Authority, or the Declaration issued in corresponding IA No. PCT/US2012/065014 dated Feb. 15, 2013.
Invitation to Pay Additional Fees issued in corresponding IA No. PCT/US2012/022162 dated Apr. 12, 2012.
Maruzen, "New Experimental Chemistry Course 1 Basic Operation I", Sep. 20, 1975, 459-463.
Yue, et al., A novel polymeric chlorhexidine delivery device for the treatment of periodontal disease, Biomaterials, vol. 25, 2004, pp. 3743-3750.
International Search Report and Written Opinion of the International Searching Authority, or the Declaration issued in corresponding IA No. PCT/US2015/034336 dated Mar. 23, 2016.
International Search Report and Written Opinion issued in corresponding IA No. PCT/US2014/025549 dated Jul. 25, 2014.
International Preliminary Reporton Patentability dated Sep. 24, 2015 issued in corresponding IA No. PCT/US2014/025549 filed Mar. 13, 2014.
International Preliminary Report on Patentability dated Jul. 23, 2013 issued in corresponding IA No. PCT/US2012/022162 filed Jan. 23, 2012.
International Search Report and Written Opinion dated Jan. 21, 2013 issued in corresponding IA No. PCT/US2012/037429 filed May 11, 2012.
International Preliminary Report on Patentability dated Nov. 19, 2013 issued in corresponding IA No. PCT/US2012/037429 filed May 11, 2012.
Pei, et al. "Plant Fiber Chemistry", pp. 244-246, China Light Industry Press, Jul. 2012.
International Preliminary Report on Patentability dated May 20, 2014 issued in corresponding IA No. PCT/US2012/065014 filed Nov. 14, 2012.
Sateesh Kandavilli: "Polymers in Transdermal Drug Delivery Systems," Pharmaceutical Technology, May 31, 2002, XP055101101, Retrieved from the internet: http://www.pharamtech.com/pharmtech/data/articiestandard/pharmtech/192002/18600/article.pdf [retrieved on Feb. 10, 2014].
Luo, et al., A Complete Collection of Pharmaceutical Excipients, Sichuan university of science and technology press, Jan. 31, 2006, 53-56.
International Preliminary Report on Patentability dated Dec. 6, 2016 issued in corresponding IA No. PCT/US2015/034336 filed Jun. 5, 2015.
He et al., General Practitioner's Guidelines for Medication Use, Beijing Science and Technology Press, Nov. 30, 2010, 1205.
Yao, Application Directory of Pharmaceutical Excipients, China Medical Science and Technology Press, Aug. 31, 2011, 1342-1347.
International Preliminary Report on Patentability dated Jul. 6, 2015 issued in corresponding IA. No. PCT/US2014/015263 filed Feb. 7, 2014.
Invitation to Pay Additional Fees dated May 22, 2014 issued in corresponding IA No. PCT/US2014/015263 filed Feb. 7, 2014.
International Preliminary Report on Patentability dated Dec. 15, 2016 issued in corresponding IA No. PCT/US2015/033689 filed Jun. 2, 2015.
Polysciences, Poly(acrylic acid), 25% soln, in water [PAA ~50,000], Retrieved Aug. 14, 2021 (Year 2021).

* cited by examiner

TRANSPARENT COVER DRESSING APPLICATION SYSTEM AND INCLUSION OF LABEL STRIP

CROSS REFERENCES TO RELATED APPLICATIONS

The present application is a 371 of International Patent Application No. PCT/US2014/025549 which was published in English on Sep. 25, 2014 and claims the benefit of U.S. Provisional Application No. 61/787,908 filed Mar. 15, 2013, both of which are incorporated herein by reference in their entireties.

FIELD

The present subject matter relates to dressings made from films which are typically oxygen permeable, and have high moisture vapor permeability but which are impermeable to liquid water and bacteria. The dressings include a label strip that can include text, indicia, logos, or other markings. The subject matter also relates to methods of producing such dressings and similar products.

BACKGROUND

Wound dressings made with composite layers of film and adhesive which have high moisture vapor transmission rates are well known in the art. These dressings are used in many applications and are beneficial in that they are impervious to bacteria and liquid water but yet allow oxygen to penetrate the dressing from the ambient atmosphere and allow moisture from the skin of the patient to escape from beneath the dressing.

In order to obtain the desired moisture vapor transmission rate, the dressings are made from extremely thin films of polyurethane or of other polymeric materials which have the desired moisture vapor transmission properties. These films are extremely thin, typically less than 10 mils, and are very flexible, limp, and flimsy because of their thinness. These characteristics allow the dressing to be applied to the varying contours of the human body but also present difficulties in the application of the dressing to a patient. The dressings are typically provided with a release sheet covering the adhesive surface of the dressing. The release sheet is removed from the dressing when the dressing is applied to the patient. The thinness of the film and its flexibility allows the film to turn over onto itself during attempts to apply the film dressing to a patient. The film is similar in this property to polyvinylidene chloride film household wrap. When a portion of the adhesive surface of the film touches other portions of the adhesive surface, the film dressing sticks to itself and makes it extremely difficult to separate the adhered portions and then apply to the patient.

In order to overcome this problem, film dressings of this type have been provided with adhesive-free tabs at opposite ends of the film. In some products there is a reinforcing member at the tab ends to provide a grasping or holding surface to be used to apply the dressings to a patient.

Prior to or after application of a dressing or other adhesive thin film article to a patient, it may in certain applications be necessary to mark or otherwise apply text or information to the dressing. For example, for certain dressings, date information associated with the article may be included. In other instances, it may be desirable to include patient information or treatment information directly on the dressing or article. Although a medical practitioner could in certain instances, write or otherwise apply markings along an outer face of the dressing that practice may be undesirable. The outer face of the polyurethane film or other polymeric material may be difficult to write upon. Other parameters may detrimentally impact ability to write or apply markings on the dressing.

Accordingly, a need exits for a dressing or thin film article which may readily receive text or other markings or indicia.

SUMMARY

The difficulties and drawbacks associated with previously known dressings are addressed in the present articles and related methods.

In one aspect, the present subject matter provides a dressing comprising a dressing film defining an inner face and an oppositely directed outer face. The dressing also comprises a support film disposed on at least a portion of the outer face of the dressing. The dressing additionally comprises an adhesive disposed on at least a portion of the inner face of the dressing film. And, the dressing also comprises a label strip adhered to the outer face of the dressing film. The label strip has an outer face adapted to receive printing, marking, or other indicia.

As will be realized, the subject matter described herein is capable of other and different embodiments and its several details are capable of modifications in various respects, all without departing from the claimed subject matter. Accordingly, the drawings and description are to be regarded as illustrative and not restrictive.

DETAILED DESCRIPTION OF THE EMBODIMENTS

Figure 1:
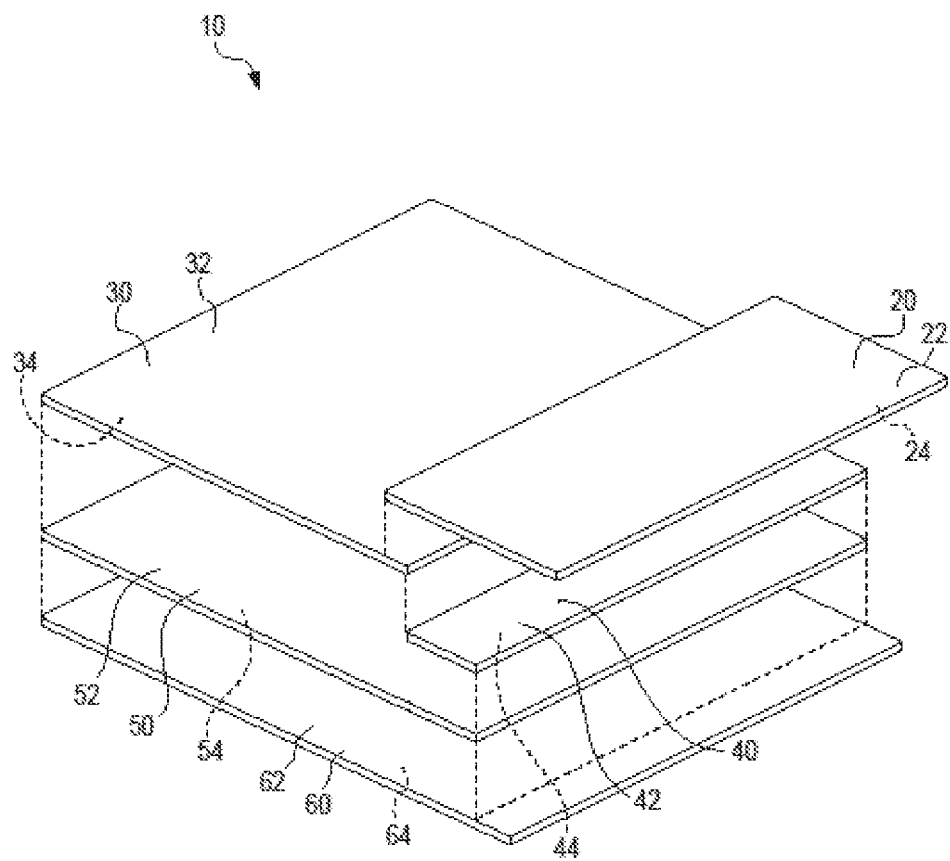
FIG. 1 is a perspective, schematic exploded assembly view of a dressing having a label strip in accordance with the present subject matter.

The present subject matter provides dressings which include one or more label strips. The label strip can include text, indicia, logos, or other markings. The label strip is incorporated into a transparent cover dressing such as a window dressing, or any dressing using a thin polymeric film (such as for example polyurethane) having an adhesive on a face of the film, for contacting skin. In certain embodiments of the present subject matter, the label strip is attached to an outer face of the transparent film. Attachment can be accomplished by a variety of techniques, however, attachment is typically achieved by adhesive. After application of the dressing to skin, the label remains attached to the outer face of the transparent film. Prior to (or after) application, writing or other operations can be performed to provide text or information on the label strip, which will remain with the dressing even after application.

The dressings generally comprise (i) an outer support film, (ii) one or more handling tabs attached to the support film, (iii) a thin dressing film, (iv) one or more adhesives on a face of the dressing film, (v) a liner covering the one or more adhesives prior to use or application of the dressing, and (vi) one or more label strips incorporated in the dressing and typically disposed on an outer face of the dressing film.

Details as to each of the components of the dressings are as follows.

Support Film

Transparent or translucent film materials are particularly intended as supporting films. However, opaque or non-transparent paper or film materials can be used alternatively. Useful as supporting films are particularly those films that are manufactured from polyester, polyethylene, polypropylene, polyvinylchloride, polystyrene, polyamide, polycarbonate, cellulose ester, ethylene vinyl acetate, polyvinyl acetate, polyvinyl alcohol and/or combinations thereof. Particularly preferred are supporting films from polyester or polyethylene or polypropylene. The present subject matter also includes the use of paper or paper-based materials for the support component. Combinations of polymeric and paper materials can also be used. It has been proven to be particularly preferable when the thickness of the supporting films are adjusted to a thickness of about 15 to about 80 µm, particularly from about 20 to about 60 µm and especially from about 20 to about 40 µm.

Handling Tabs

One or more optional handling tab(s) may be incorporated into the dressing and is provided either partially or entirely along an edge of the dressing and/or the support film. Handling tabs can be provided on the support film, the release liner, or both. When provided on the support film, the handling tab can be in the form of an integral extension or projection of the support film. In certain versions, the handling tab is arranged near the center of a side edge of the dressing. However, the handling tab can have various other configurations and arrangements. Also, the location can be as desired and more than one handling tab can be provided.

Dressing Film

The dressing film is preferably made of a thin, flexible, conformable, resilient, supple, limp or flimsy material that can flex or bend to conform to irregular surfaces or contours, such as those of anatomical body parts. Preferably, dressing film is sufficiently resilient to stretch or flex in response to movement or flexing of the dressing support film and to conform to the dressing support film when the dressing support film returns to an unflexed condition. The dressing film is preferably transparent or substantially transparent to permit visualization through the dressing film and/or of the support film. Or, the dressing film can be opaque. The dressing film can be air permeable to allow oxygen to penetrate the dressing as well as moisture vapor permeable to allow moisture from the skin surface to escape through the dressing, and the dressing film can be liquid, air and bacteria impermeable. Non limiting examples of materials suitable for the dressing film include polymeric materials, such as polyurethane, copolyester, elastomeric polyester, polyethylene, blends of polyurethane and polyester, chlorinated polyethylene, styrene/butadiene block copolymers and polyvinyl chloride, formed into continuous films or sheets by casting, extrusion or other processes. The dressing film can have various sizes and configurations dependent on the surfaces to which the dressing is to be applied. The dressing film may have a square or rectangular peripheral configuration with rounded or radiused corners. The present subject matter includes nearly any shape for the dressing film. The dressing film preferably has a minimal thickness, typically in the range of 0.0005 inch to 0.004 inch, preferably about 0.0015 inch, with conformability of the dressing increasing with decreasing thickness of the dressing film.

Adhesives

Adhesive is provided on a skin contacting side or face of the dressing film to cover at least the entire area circumscribed by the final dressing portion and, preferably, for ease of manufacturing adhesive covers the entire area of face of the dressing film including a peripheral backing portion. Adhesive can be provided on a face of the dressing film in many various ways including solvent spreading, spraying, coating and extrusion, for example, and the adhesive can be applied directly to the dressing film or indirectly via a carrier sheet. The adhesive utilized is preferably a pressure sensitive, skin contact adhesive that is preferably hypo-allergenic and non-irritating to skin. Representative non-limiting examples of materials suitable for the adhesive include acrylate copolymers, such as copolymers of 2-ethylhexylacrylate and vinyl acetate with or without a cross-linking agent, water based adhesives and hot melt adhesives, for example. If desired, various medicaments and/or antimicrobial agents can be included in the adhesive to promote healing and inhibit infection. The adhesive is preferably applied on a face of the dressing film in a thin layer, such as on the order of 0.001 inch to 0.010 inch in thickness or greater (according to the desired application), sufficient to obtain adequate skin adhesion without impairing the air and moisture vapor transmission characteristics of the dressing. Preferably, the adhesive is an acrylic adhesive.

Release Liner

Various materials can be utilized for the release liner including conventional smooth surface paper materials, polyester films and polyolefin films of the type typically utilized as release liners, such as, for example, kraft paper, polyethylene, polypropylene, polyester and composites thereof. In certain applications, the release liner is sufficiently thick, i.e., on the order of 0.004 inch to 0.0075 inch in thickness or higher, to rigidify a backing sheet prior to use. The release liner is preferably sufficiently rigid and/or thick to typically maintain a flat configuration. However, the release liner can have some flexibility to bend, flex or deform in response to external pressure. Depending on the material utilized for the release liner, the surface can be coated with a release agent, such as fluorochemicals or silicone, for example, to facilitate release of the liner portion from the adhesive of the final dressing. It will be appreciated that the material utilized for the release liner, with or without a release agent, can be varied to achieve a desired bond or tenacity of adhesion between the release liner and the adhesive and that the bond or tenacity of adhesion can be selected such that manual removal or peeling away of the liner portion from the backing sheet can be accomplished with a gentle pressure or pulling force and without damage to or impairment of the dressing.

The liner can be a single panel liner or include multiple components or panels to form a liner assembly.

Label Strips

A wide range of materials can be used for the label strips that are associated with the dressings. In certain embodiments, the label strips are formed from paper or paper based materials. However, the present subject matter includes forming the label strips from polymeric materials. It is also contemplated that the label strips can be formed from combinations of paper and polymeric materials and be in the form of composite materials. The present subject matter also includes forming the label strips with one or more regions or layers of paper material(s) and one or more regions or layers of polymeric materials. Furthermore, one or both faces of the label strip and particularly a print-receiving face can be coated with a print-receptive topcoat to promote ink adherence or ink "wet-out." Moreover, one or both faces of the label strip could be subjected to a surface treatment operation such as corona treatment or plasma treatment.

The label strip can also be coated with a release coating so that an adhesive coated portion of the handling tab can extend over the label strip. This configuration provides extra support to the dressing on application (and before removal of the support layer and associated handling tab). In this case the release coating is chosen to prevent permanent or strong adhesion of the handling tab and to provide significant "wet out" for the ink to allow writing/printing on the tab.

The one or more label strip(s) are typically disposed on an outer face of the dressing film. The label strip(s) can be secured to the dressing film such as by adhesive. The label strip(s) in certain versions of the dressings, are provided immediately alongside a recessed side edge of a support film. In particular versions of the dressings, the label strip(s) are positioned under the handling tab(s). And in specific versions of the present subject matter, the label strip(s) are disposed between a handling tab the dressing film, and also immediately alongside an edge of a support film. However, it will be understood that the present subject matter includes a wide range of arrangements, configurations, and variations of the dressings described herein.

Figure 2:
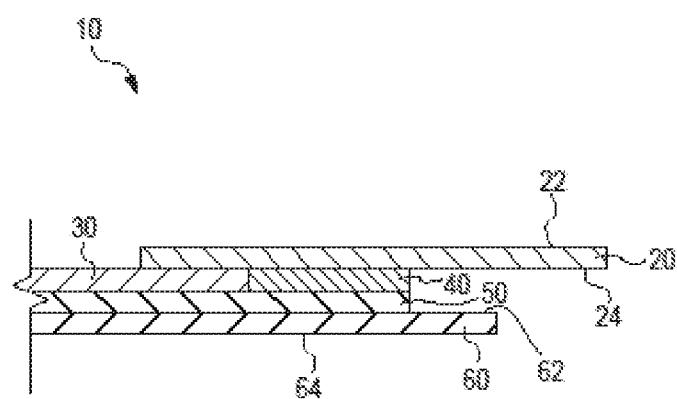
FIG. 2 is a schematic cross section of an end region of the dressing in FIG. 1, illustrating the label strip in greater detail.

FIGS. 1 and 2 illustrate a dressing 10 in accordance with the present subject matter. The dressing 10 comprises a handling tab 20, a support film 30, a label strip 40, a dressing film 50, and a release liner 60. The handling tab 20 defines an outer face 22 and an oppositely directed inner face 24. The support film 30 defines an outer face 32 and an oppositely directed inner face 34. In the particular version of dressing 10 depicted in FIG. 1, the handling tab 20 is adhesively attached to a peripheral edge region of the outer face 32 of the support film 30. The label strip 40 also defines an outer face 42 and an oppositely directed inner face 44. The outer face 42 receives text, markings, and/or indicia as described herein. The label strip 40 is disposed on an outer face 52 of the dressing film 50. In the particular version of dressing 10 shown, the label strip 40 is oriented parallel to and immediately alongside a recessed edge of the support film 30. A thin layer or coating of adhesive (not shown) resides on an inner face 54 of the dressing film 50. The release liner 60 covers the adhesive, and specifically a release coated face 62 of the liner 60 contacts the adhesive layer on the inner face 52 of the dressing film 50. The release liner 60 also defines an outer face 64 which is opposite the release coated face 62. In the particular version of the dressing 10 depicted in FIG. 1, a side edge or peripheral edge portion of the liner 60 extends outward beyond a corresponding edge of the dressing film 50, and in certain versions also beyond a corresponding edge of the label strip 40. The release liner edge may or may not extend beyond the handling tab 20. In the version of dressing 10 depicted in FIG. 1, the handling tab 20 extends further beyond the corresponding edge of the liner 60.

FIG. 2 is a schematic cross sectional view of an edge portion of the dressing 10 depicted in FIG. 1. FIG. 2 illustrates a particular version of the dressing 10 in which the handling tab 10 extends beyond a corresponding edge region of the liner 60, and the liner 60 extends beyond corresponding edge regions of the label strip 40 and the dressing film 50.

Figure 3:
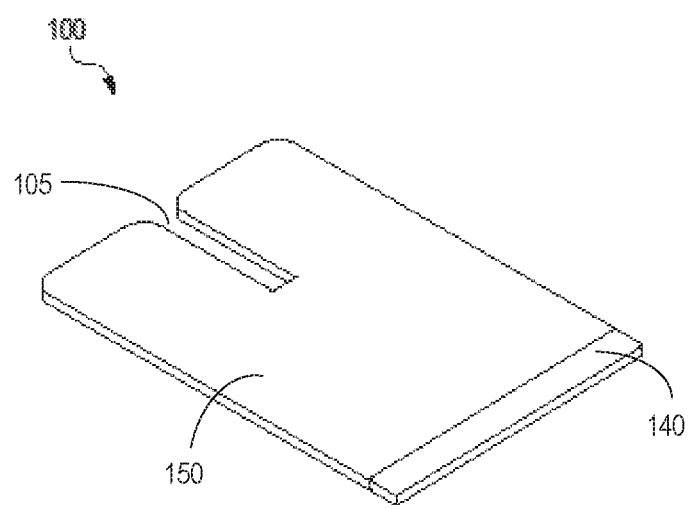
FIG. 3 is a perspective, schematic view of another dressing having a label strip in accordance with the present subject matter.

FIG. 3 is a perspective view of another dressing 100 in accordance with the present subject matter. In this version, the dressing 100 defines an interior slot or access region 105. This configuration is typical for certain dressings used to cover body apertures for IV tubes, typically referred to as peripheral IV (PIV) dressings. The dressing 100 includes a dressing film 150 and a label strip 140 extending along an edge of the dressing. FIG. 3 illustrates the dressing 100 after application such as to a patient (not shown), and removal of a support film (not shown) that would otherwise cover the dressing film 150, and removal of handling tabs (not shown) that were attached to the support film.

Many other benefits will no doubt become apparent from future application and development of this technology. For example, the label strip can add additional bulk to the limp flimsy film to facilitate removal of the dressing from the skin after use. Due to the low caliper of the dressings it is typically very difficult to get a starting point for removal. The extra thickness and stiffness at the label strip position can significantly assist or promote removal efforts.

All patents, published applications, and articles noted herein are hereby incorporated by reference in their entirety.

As described hereinabove, the present subject matter solves many problems associated with previous strategies, systems and/or devices. However, it will be appreciated that various changes in the details, materials and arrangements of components, which have been herein described and illustrated in order to explain the nature of the present subject matter, may be made by those skilled in the art without departing from the principle and scope of the claimed subject matter, as expressed in the appended claims.

What is claimed is:

1. A dressing comprising:
  a dressing film defining an inner face and an oppositely directed outer face;
  a support film disposed on at least a portion of the outer face of the dressing;
  an adhesive disposed on at least a portion of the inner face of the dressing film; and
  a label strip adhered to the outer face of the dressing film, the label strip having an outer face adapted to receive printing, marking, or other indicia; and
  at least one handling tab disposed on and attached to the support film;
  wherein an the label strip is disposed immediately alongside an recessed edge of the support film; and
  wherein the label strip remains attached to the dressing film after application of the dressing.

2. The dressing of claim 1 further comprising:
  a release liner covering the adhesive.

3. The dressing of claim 2 wherein an edge of the release liner extends beyond a corresponding edge of the dressing film.

4. The dressing of claim 2 wherein an edge of the release liner extends beyond a corresponding edge of the label strip.

5. The dressing of claim 1 wherein the label strip includes paper.

6. The dressing of claim 1 wherein the dressing film includes polyurethane.

7. The dressing of claim 1 wherein the support film includes a material selected from the group consisting of paper, polymeric materials, and combinations thereof.

8. The dressing of claim 1 wherein an edge of the handling tab extends beyond a corresponding edge of the support film.

9. The dressing of claim 1 wherein an edge of the handling tab extends beyond a corresponding edge of the label strip.

10. The dressing of claim 1 wherein an edge of the handling tab extends beyond a corresponding edge of the dressing film.

11. The dressing of claim 1 wherein an edge of the handling tab extends beyond a corresponding edge of the release liner.

* * * * *